United States Patent [19]

Cliffe

[11] Patent Number: 5,204,470
[45] Date of Patent: Apr. 20, 1993

[54] AZABICYCLIC DERIVATIVES

[75] Inventor: Ian A. Cliffe, Slough, England

[73] Assignee: John Wyeth & Brother, Limited, Miadenhead, England

[21] Appl. No.: 756,648

[22] Filed: Sep. 9, 1991

[30] Foreign Application Priority Data

Sep. 12, 1990 [GB] United Kingdom ................ 9019973

[51] Int. Cl.$^5$ ............................................ C07D 451/02
[52] U.S. Cl. .................................... 546/126; 540/593; 544/238; 544/333; 544/405; 546/108; 546/112; 546/125
[58] Field of Search ................ 514/304; 546/126, 125, 546/108, 112; 540/593; 544/238, 333, 405

[56] References Cited

U.S. PATENT DOCUMENTS 3,133,073  5/1964  Archer ................................ 546/125
4,929,625  5/1990  Cliffe ................................... 514/304

Primary Examiner—Bernard Dentz
Attorney, Agent, or Firm—Arthur G. Seifert

[57] ABSTRACT

Azabicyclic compounds of formula

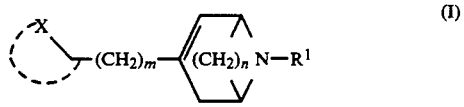
(I)

and their pharmaceutically acceptable acid addition salts are disclosed. In the formula,

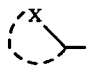

is an optionally substituted heteroaryl group containing at least one hetero atom X; n is 2, 3 or 4; m is 1 or 2; $R^1$ is hydrogen, $C_{1-6}$ alkyl, $C_{3-5}$-alkenyl, $C_{3-6}$ cycloalkyl, $C_{3-6}$ cycloalkyl-$C_{1-2}$ alkyl or aryl- or heteroaryl-$C_{1-2}$-alkyl; and the —$(CH_2)_m$

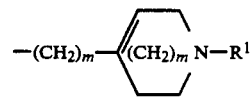

moiety is ortho to the hetero atom X. The compounds exhibit activity as 5-HT$_3$-antagonists and can be used, inter alia, for the treatment of neuropsychiatric disorders.

8 Claims, No Drawings

AZABICYCLIC DERIVATIVES

This invention relates to azabicyclic derivatives. In particular the invention relates to novel azabicyclic derivatives to processes for their preparation, their use and to pharmaceutical compositions containing them. The compounds are useful as antagonists of specific 5-hydroxytryptamine (5-HT) receptors as explained hereinbelow.

The novel azabicyclic derivatives of the present invention are compounds of the general formula (I)

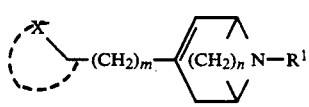
(I)

and the pharmaceutically acceptable acid addition salts thereof. wherein

represents an optionally substituted heteroaryl group containing at least one hetero atom X selected from the group consisting of nitrogen, oxygen and sulphur; n represents 2,3 or 4, m represents 1 or 2, $R^1$ is hydrogen, $C_{1-6}$-alkyl, $C_{3-5}$-alkenyl, $C_{3-6}$-cycloalkyl, $C_{3-6}$-cycloalkyl-$C_{1-2}$alkyl or aryl- or heteroaryl-$C_{1-2}$-alkyl (where the aryl group is a phenyl or napthyl radical optionally substituted by one or more halogen, $C_{1-4}$-alkoxy or $C_{1-4}$-alkyl groups and the heteroaryl group is a mono- or bicyclic heteroaryl radical containing 5 to 12 ring atoms and one or two hetero atoms selected from oxygen, nitrogen and sulphur); and the

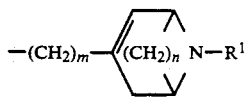

moiety is ortho to the hetero atom X.

Preferably the heteroaryl radical

contains 5 to 12 ring atoms including one to three hetero atoms selected from oxygen, nitrogen and sulphur and is optionally substituted by for example one or more $C_{1-4}$alkyl, $C_{1-4}$alkoxy, amino, $C_{1-4}$alkylamino, di($C_{1-4}$-alkyl)amino, halogen preferably fluorine or chlorine), trifluoromethyl, phenyl, halophenyl, $C_{1-4}$-alkylphenyl, $C_{1-4}$-alkoxyphenyl, carboxy, carboxamido, nitro, thiol, $C_{1-4}$-alkylthio or $C_{1-4}$-alkoxycarbonyl substituents.

Examples of such optionally substituted heterocycles include 5 membered heterocycles with one hetero atom (e.g. furan, pyrrole and thiophene) which may be ring fused to, for example, a benzene or cyclohexane ring (e.g. benzo(b)furan, benzo(c)furan, indole, benzothiophene); 5-membered heterocycles having two heteroatoms in 1,2 or 1,3-positions which may be ring fused to other rings (e.g. oxazoles, pyrazoles, imidazoles, thiazoles, benzimidazoles, benzoxazoles, purines); 5-membered heterocycles with three heteroatoms which may be ring fused to other rings (e.g. triazoles, benzotriazoles, oxadiazoles); 6-membered heterocycles with one heteroatom and which may be ring fused to other rings (e.g. pyridine, quinoline, isoquinoline, phenanthridine, 5,6-cycloheptenopyridine, 5,6-cyclohexenopyridine); 6-membered heterocycles with two heteroatoms which may be ring fused to other rings (e.g. pyridazines, cinnolines, phthalazines, pyrazines, quinoxalines, pyrimidines, quinazolines); 6-membered heterocycles with three heteroatoms (e.g. 1,3,5-triazine), 7-membered heterocycles which may be fused to other rings (e.g. benzodiazepines).

Preferred

groups include 2-pyridyl optionally substituted by, for example, chloro, nitro, $C_{1-4}$-alkyl or carboxamido; 2- or 4- pyrimidyl optionally substituted by for example chloro, amino, or $C_{1-4}$-alkoxy; 2-pyrazinyl optionally substituted by, for example, halo or $C_{1-4}$-alkyl; 2-pyridazinyl optionally substituted by, for example, halo or $C_{1-4}$-alkoxy; 2-quinolinyl or 1-isoquinolinyl optionally substituted by, for example, $C_{1-4}$-alkyl, $C_{1-4}$ alkoxy or halo; 2-thienyl; 2-benzo(b)thienyl; 1H-indazol-3-yl optionally subsituted by, for example, nitro or $C_{1-4}$ alkyl; 2-benzoxazolyl; 2-benzothiazolyl; and 6-phananthridinyl.

Preferably $R^1$ is $C_{1-4}$ alkyl, particularly methyl.

Preferably n is 2.

The compounds in which $R^1$ is methyl and n is 2 are dehydrotropane derivatives.

Preferably m is 1.

The compounds of the invention contain an asymmetric carbon atom so that the compounds of the invention can exist in different stereoisomeric forms. The compounds can, for example, exist as racemates or optically active forms. Furthermore the compounds of general formula (II) below can exist in two different configurations corresponding to the endo configuration as in tropine and the exo configuration as in pseudotropine. The endo configuration is preferred.

In the compounds of formula I, any alkyl group is preferably methyl, ethyl, propyl or butyl; any alkoxy group is preferably methoxy, ethoxy or propoxy; an alkenyl group is preferably allyl or methallyl; a cycloalkyl is preferably cyclopentyl or cyclohexyl; cycloalkylalkyl is preferably cyclopentylmethyl or cyclohexylmethyl; arylalkyl is preferably benzyl; and cycloalkylalkyl is preferably cyclopentylmethyl or where the $R^1$ group contains a heteroaryl radical this may be any one of the heteroaryl groups mentioned above in connection with the

radical.

The compounds of the invention may be prepared by methods known in the art.

For example, the compounds of the invention may be prepared by dehydrating an alcohol compound of formula

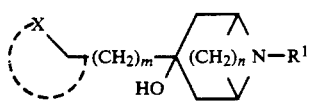

(II)

or an acid addition salt thereof (where m, n,

and $R^1$ have the meanings given above). The dehydration may be carried out using known dehydrating agents e.g. polyphosphoric acid, thionyl chloride or acetic anhydride. The dehydration may result in a mixture of isomer which can be separated by, e.g., chromatography.

The alcohols of formula (II) and their acid addition salts are novel compounds, which are also provided by the present invention. The acid addition salt is preferably a pharmaceutically acceptable acid addition salt. The compounds may be prepared by reacting a heterocyclic compound of formula

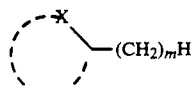

(III)

with a strong base and a ketone of formula

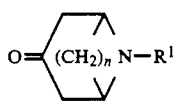

(IV)

(where

m, n and $R^1$ have the meanings given above). The strong base forms the anion of the compound (III). Examples of suitable strong bases include potassium or sodium hydride, phenyl- or alkyl-lithiums (e.g. butyllithium), and alkali metal amides (e.g. lithium disopropylamide).

The compounds of formula (III) and (IV) are known or can be prepared by methods known in the art for analogous compounds.

It will be realised that if any of the reactants (II), (III) or (IV) contains groups that would be affected under the reaction conditions employed in the reactions the group may be protected and the protecting group subsequently removed. For example hydroxy groups may be protected by formation of acetals or ethers (e.g. benzyl or silyl ethers) and amino groups may be protected by formation of urethanes or N-benzyl derivatives.

In addition, any substituent present in the final compound of formula (I) may be removed or replaced by another substituent using methods that are known in the art. For example a chloro substituent on the heteroaromatic ring may be removed by catalytic hydrogenation or an alkoxycarbonyl substituent may be reduced to hydroxymethyl.

If in the processes described above the compound of the invention is obtained as an acid addition salt, the free base can be obtained by basifying a solution of the acid addition salt. Conversely, if the product of the process is a free base, an acid addition salt, particularly a pharmaceutically acceptable acid addition salt may be obtained by dissolving the free base in a suitable organic solvent and treating the solution with an acid, in accordance with conventional procedures for preparing acid addition salts from base compound.

Examples of acid addition salts are those formed from inorganic and organic acids, such as sulphuric, hydrochloric, hydrobromic, phosphoric, tartaric, fumaric, maleic, citric, acetic, formic, methanesulphonic, and p-toluenesulphonic, acids.

The compounds of the present invention possess pharmacological activity. In particular they antagonise specific 5-hydroxytryptamine (5-HT) receptors in warm blooded animals. Specifically the compounds possess $5\text{-}HT_3$ antagonistic activity and hence are of value in conditions where antagonism of $5\text{-}HT_3$ receptors is desirable. Thus, the compounds are useful for the treatment of neuropsychiatric disorders (e.g. as anxiolytics, as anti-psychotics, for treating cognitive impairment and addiction) and for treating migraine or emesis and other gastro-intestinal disorders.

The compounds of the invention are tested for $5\text{-}HT_3$ receptor antagonism in the isolated vagus nerve of the rat by a method based upon that of Ireland S. J. and Tyers M. B., Brit. J. Pharmacol., 1987, 90, 229–238. The procedure relies upon the ability of 5-HT to induce depolarization of neurones in the cervical vagus nerve by a direct action on $5\text{-}HT_3$ receptors. A concentration-response curve to 5-HT induced depolarization is obtained and the antagonists are added to the bath containing the isolated nerve before repeating the 5-HT concentration-response curve. Antagonist potency is estimated for the 5-HT concentration ratios and expressed as an apparent $pK_B$ value (where $K_B$ is the antagonist dissociation constant). When tested by this procedure 3-(2-quinolinylmethyl)-8-methyl-8-azabicyclo[3.2.1]oct-2-ene, a representative compound of this invention, had a $pK_B$ of 7.2.

The compounds of the invention are also tested for $5\text{-}HT_3$ antagonist activity in the isolated right atrium of the rabbit heart based upon the method of Fozard J. R., Naunyn-Schmiedeberg's Arch. Pharmacol., 1984, 326, 36–44. This procedure relies upon the ability of 5-HT to stimulate $5\text{-}HT_3$ receptors present on symphetic nerve terminals in the heart, causing release of noradrenaline which evokes an increase in the spontaneous rate of beating. The antagonist potency is expressed in a similar manner to that of the preceding test method i.e. as an apparent $pK_B$. When tested by this procedure 3-(2-quinolinylmethyl)-8-methyl-8-azabicyclo[3.2.1]oct-2-ene, a representative compound of this invention, had a $pK_B$ of 8.6.

The invention further provides a compound of formula (I) or a pharmaceutically acceptable acid addition salt thereof for use in antagonising $5\text{-}HT_3$ receptors in a mammal.

The invention also provides a pharmaceutical composition comprising a compound of the invention in association with a pharmaceutically acceptable carrier. Any suitable carrier known in the art can be used to prepare the pharmaceutical composition. In such a composition, the carrier is generally a solid or liquid or a mixture of a solid and a liquid.

Solid form compositions includes powders, granules, tablets, capsules, (e.g. hard and soft gelatin capsules), suppositories and pessaries. A solid carrier can be, for example, one or more substances which may also act as flavouring agents, lubricants, solubilisers, suspending agents, fillers, glidants, compression aids binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99%, e.g. from 0.03 to 99%, preferably 1 to 80% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

The term "composition" is intended to include the formulation of an active ingredient with encapsulating material as carrier to give a capsule in which the active ingredient (with or without other carriers) is surrounded by the carrier, which is thus in association with it. Similarly cachets are included.

Liquid form compositions include, for example, solutions, suspensions, emulsions, syrups, elixirs and pressurised compositions. The active ingredient, for example, can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solibilizers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration incude water )particularly containing additives as above e.g. cellulose derivatives, preferably sodium carboxymethyl cellulose solution), alcohols (including monohydric alcohols and polyhydric alcohols e.g. glycerol and glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilised by, for example, intramuscular, intraperitoneal or subcutaneous injection. Sterile solutions can also be administered intravenously. When the compound is orally active it can be administered orally either in liquid or solid composition form.

The compounds of the invention can also be administered by the nasal route. When formulated for nasal administration the compositions may comprise a compound of the invention in an liquid carrier; such compositions may be administered for example in the form of a spray or as drops. The liquid carrier may be water (which may contain further components to provide the desired isotonicity and viscosity of the composition). The composition may also contain additional excipients such as preservatives, surface-active agents and the like. The compositions may be contained in a nasal applicator that enables the composition to be administered as drops or as a spray. For administration from an aerosol container the composition should also include a propellant.

Preferably the pharmaceutical composition is in unit dosage form, e.g. as tablets or capsules. In such form, the composition is sub-divided in unit doses containing appropriate quantities of the active ingredient; the unit dosage forms can packaged compositions, for example packeted paowders, vials, ampoules, prefilled syringes or sachets containing liquids. The unit dosage form can be, for example, a capsule or tablet itself, or it can be the appropriate number of any such compositions in packaged form. The quantity of the active ingredient in unit dose of composition may be varied or adjusted form 0.5 mg or less to 750 mg or more, according the particular need and the activity of the active ingredient.

The following Examples illustrate the invention:

EXAMPLE 1

8-Methyl-3-(2-quinolinylmethyl)-endo-8-azabicyclo 3.2.1]octan-3-ol

A stirred solution of 2-methylquinoline (10 ml, 73.9 mmol) in dry THF (80 ml) at 0° was treated dropwise over 10 min with 1.5 M-butyllithium in hexane (53 ml, 79.5 mmol) under an atmosphere of nitrogen, after 1 h treated dropwise with a solution of tropinone (10 g, 71.8 mmol) in dry THF (80 ml), warmed to room temperature, after 1 h treated with water (100 ml), concentrated in vacuo to a volume of roughly 100 ml, and extracted with ethyl acetate (2×150 ml). The extracts were washed with water (100 ml), dried (MgSO$_4$), and evaporated in vacuo. The residue was purified by chromotography (alumina, ethyl acetate) to give the product as a yellow oil (8.54 g). The hygroscopic dihydrochloride salt was isolated as a foam from ether-methanol-hydrogen chloride.

Found: C, 58.6; H, 7.0; N, 7.6;

$C_{18}H_{22}N_2O.2HCl$ ¾$H_2O$ requires C, 58.7; H, 7.4; N, 7.1%.

EXAMPLE 2

3-(2-Quinolinylmethyl)-8-methyl-8-azabicyclo[3.2.-1]oct-2-ene

An emulsion of the product from example 1 (3.96 g, 14.0 mmol) in polyphosphoric acid (25 g) was heated at 115° for 22 h, poured into water (200 ml), basified with 33% aqueous ammonia, and extracted with ethyl acetate (2×200 ml). The extracts were washed with water (50 ml), dried (MgSO$_4$), and evaporated in vacuo to give a brown oil which was purified by chromatography (alumina; ether). The yellow oil was converted into the dihydrochloride salt with methanol-ethereal hydrogen chloride. Recrystallisation from methanol-ethyl acetate gave the product dihydrochloride salt (0.74 g) as an hygroscopic solid. The sample was too hygroscopic to obtain an accurate melting point.

Found: C, 58.4; H, 6.9; N, 7.4. $C_{18}H_{20}N_2.2$ HCl.1.75 $H_2O$ requires C,58.6; H, 7.0; N, 7.6%.

I claim:

1. An azabicyclic compound of formula

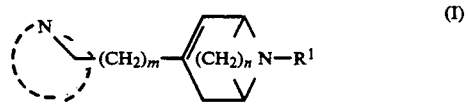

(I)

or a pharmaceutically acceptable acid addition salt thereof, wherein

represents an N-heteroaryl group containing 5 to 12 ring atoms and 0-2 other heteroatoms selected from the group consisting of N, O and S, optionally substituted by one or more $C_{1-4}$alkyl, $C_{1-4}$alkoxy, amino, $C_{1-4}$alkylamino, di($C_{1-4}$-alkyl)amino, halogen, trifluoromethyl, phenyl, halophenyl, $C_{1-4}$-alkylphenyl, $C_{1-4}$-alkoxyphenyl, carboxy, carb oxamido, nitro, thiol, $C_{1-4}$-alkylthio or $C_{1-4}$-alkoxycarbonyl substituents;

n represents 2, 3 or 4;
m represents 1 or 2;
$R^1$ is hydrogen, $C_{1-6}$-alkyl, $C_{3-5}$-alkenyl, $C_{3-6}$-cycloalkyl, $C_{3-6}$-cycloalkyl-$C_{1-2}$alkyl or aryl- or heteroaryl-$C_{1-2}$-alkyl, where the aryl group is a phenyl or napthyl radical optionally substituted by one or more halogen, $C_{1-4}$-alkoxy or $C_{1-4}$-alkyl groups and the heteroaryl group is a mono- or bicyclic heteroaryl radical containing 5 to 12 ring atoms and one or two hetero atoms selected from oxygen, nitrogen and sulphur, and

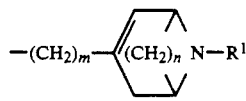

moiety is ortho to the hetero atom X.

2. A compound as claimed in claim 1 wherein

is 2-pyridyl optionally substituted by chloro, nitro, $C_{1-4}$alkyl or carboxamido, 2- or 4-pyrimidyl optionally substituted by chloro, amino, or $C_{1-4}$alkoxy; 2-pyrazinyl optionally substituted by halo or $C_{1-4}$alkyl; 2-pyridazinyl optionally substituted by halo or $C_{1-4}$alkoxy; 2-quinolinyl or 1-isoquinolinyl optionally substituted by $C_{1-4}$alkyl, $C_{1-4}$alkoxy or halo; 1H-indazol-3-yl optionally substituted by nitro or $C_{1-4}$alkyl; 2-benzoxazolyl; 2-benzothiazolyl; or 6-phenanthridinyl.

3. A compound as claimed in claim 1 wherein

is 2-quinolinyl.

4. A compound as claimed in claim 1 wherein $R^1$ is $C_{1-4}$alkyl.

5. A compound as claimed in claim 1 wherein n is 2.

6. A compound as claimed in claim 1 wherein m is 1.

7. A compound as claimed in claim 1 which is 3-(2-quinolinylmethyl)-8-methyl-8-azabicyclo[3.2.1]oct-2-ene or a pharmaceutically acceptable salt thereof.

8. A process for preparing an azabicyclic compound of formula

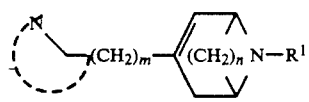 (I)

or a pharmaceutically acceptable acid addition salt thereof, wherein

represents an N-heteroaryl group containing 5 to 12 ring atoms and 0-2 other heteroatoms selected from the group consisting of N, O and S, optionally substituted by one or more $C_{1-4}$alkyl, $C_{1-4}$alkoxy, amino, $C_{1-4}$alkylamino, di($C_{1-4}$-alkyl)amino, halogen, trifluoromethyl, phenyl, halophenyl, $C_{1-4}$-alkylphenyl, $C_{1-4}$-alkoxyphenyl, carboxy, carb oxamido, nitro, thiol, $C_{1-4}$-alkylthio or $C_{1-4}$-alkoxycarbonyl substituents;

n represents 2, 3 or 4;
m represents 1 or 2;
$R^1$ is hydrogen, $C_{1-6}$-alkyl, $C_{3-5}$-alkenyl, $C_{3-6}$-cycloalkyl, $C_{3-6}$-cycloalkyl-$C_{1-2}$alkyl or aryl- or heteroaryl-$C_{1-2}$-alkyl, where the aryl group is a phenyl or napthyl radical optionally substituted by one or more halogen, $C_{1-4}$-alkoxy or $C_{1-4}$-alkyl groups and the heteroaryl group is a mono- or bicyclic heteroaryl radical containing 5 to 12 ring atoms and one or two hetero atoms selected from oxygen, nitrogen and sulphur; and

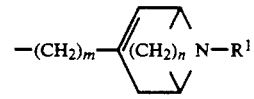

moiety is ortho to the hetero atom N, which process comprises dehydrating a compound of formula

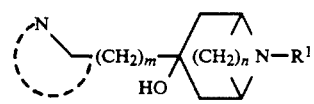 (II)

or an acid addition salt thereof, wherein m, n,

and $R^1$ are as defined above.

* * * * *